United States Patent [19]
Kehr et al.

[11] Patent Number: 6,099,467
[45] Date of Patent: Aug. 8, 2000

[54] DEVICE FOR POSITIONING COMPONENTS WITHIN ENDOSCOPIC SYSTEMS

[75] Inventors: Ulrich Kehr, Ostfildern; Jürgen Rudischhauser, Tuttlingen; Jan Dahmen, Seitingen, all of Germany

[73] Assignee: Karl Storz GmbH & Co. KG, Germany

[21] Appl. No.: 09/201,235

[22] Filed: Nov. 30, 1998

Related U.S. Application Data

[63] Continuation of application No. PCT/EP98/01825, Mar. 27, 1998.

[51] Int. Cl.[7] .................................................. A61B 1/06
[52] U.S. Cl. .......................... 600/167; 600/112; 600/162; 359/822
[58] Field of Search ..................... 600/106, 112, 600/131, 146, 162, 167, 173; 359/383, 384, 513, 694, 822, 823, 824, 825, 826, 903; 335/306; 310/75 D; 396/144; 464/29

[56] References Cited

U.S. PATENT DOCUMENTS

| | | | |
|---|---|---|---|
| 4,846,154 | 7/1989 | MacAnally et al. | 600/171 |
| 4,862,199 | 8/1989 | Centkowski et al. | 396/19 |
| 5,156,141 | 10/1992 | Krebs et al. | 600/112 |
| 5,204,572 | 4/1993 | Ferreira | 310/156 |
| 5,575,757 | 11/1996 | Kennedy et al. | 600/167 |
| 5,902,185 | 5/1999 | Kubiak et al. | 464/29 |
| 5,978,161 | 11/1999 | Lemke | 359/824 |

*Primary Examiner*—Linda C. M. Dvorak
*Assistant Examiner*—Brad C. Blaise
*Attorney, Agent, or Firm*—St. Onge Steward Johnston & Reens LLC

[57] ABSTRACT

A device for positioning components within endoscopic systems comprises a hermetically sealed housing. An outer ring element is mounted to rotate about the outer side of said housing and carries on its circumference at least one outer magnet. Further, an inner ring element is mounted inside said housing and carries likewise at least one inner magnet, said magnets being aligned in such a way that any rotation of said outer ring element has the effect to move said at least one inner magnet by magnetic coupling, such movement serving the purpose to position said respective components.

In order to achieve a simple, relatively small and functionally safe structure it is proposed that both, said outer and said inner ring elements be configured as axially non-displaceable rings carrying said oppositely arranged magnets, and that said inner ring be mechanically connected with said component to be positioned.

12 Claims, 3 Drawing Sheets

DEVICE FOR POSITIONING COMPONENTS WITHIN ENDOSCOPIC SYSTEMS

This application is a continuation of pending international application PCT/EP98/01825 filed on Mar. 27, 1998, and designating the United States.

BACKGROUND OF THE INVENTION

The present invention relates to a device for positioning components within endoscopic systems, having a hermetically sealed housing, an outer ring element mounted to rotate about the outer side of said housing and carrying on its circumference at least one outer magnet, another inner ring element mounted inside said housing and carrying at least one inner magnet, said magnets being arranged such that any rotation of said outer ring element has the effect to move said at least one inner magnet by magnetic coupling, such movement serving the purpose to position the respective components.

A device of this kind has been known from DE 195 21 654 A1.

The term positioning as used in the context of the present invention includes axial displacement and/or circumferential displacement to bring the components into a desired position.

The term components includes, for example, optical components such as lenses in an optical head of an endoscope. An axial displacement of the system serves for focusing or adjusting the optical system. The term components also includes mechanical components, which are to be swung into and out of an optical system, such as filters, diaphragms or the like. The positioning device may be handled from the proximal end of the endoscopic system, while the component to be moved may be arranged also at the distal end and may be connected with the positioning device via some linkage.

The term endoscopic systems as used in the present invention is meant to describe endoscopes and also endoscopic camera systems.

The term hermetically sealed housing as used in the present invention is meant to describe a housing sufficiently tight to allow it to be autoclaved, for example, without any risk of humidity or liquids, i.e. contaminations, penetrating into the interior of the housing as a result of the extreme temperature variations encountered. The outer magnets of the outer ring element arranged around the outer side of the tight housing interact in the way of a magnetic coupling with the inner magnets of the inner ring element arranged inside the tight housing.

In the case of the known optical device mentioned at the outset the inner magnet is received in a helically shaped slot of a sleeve mounted stationarily inside the tight housing. A lens mount, carrying the lenses of a lens group, is mounted for axial displacement and rotation inside the sleeve. The inner magnet, being configured as a circular magnet, engages a radial blind bore provided on the outer circumference of the lens mount.

The magnet of the outer rotatable ring element is configured as a rectangular magnet that interacts with the circular magnet, i.e. is arranged substantially opposite the latter.

Rotation of the outer ring element together with the rectangular magnet causes the inner circular magnet to be rotated simultaneously. Since the circular element is received in a helically shaped slot in the sleeve, it also moves in axial direction.

Consequently, the rectangular magnet located on the outer ring must have an axial extension that corresponds to the maximum axial displacement of the inner circular magnet as it moves along the helically shaped slot in the sleeve.

The fact that the circular magnet engages a radial blind bore on the outer side of the lens mount results in the latter being axially displaced in response to the axial advance motion of the circular magnet.

This configuration is connected with the disadvantage that due to the axial mobility of the inner magnet the outer ring magnet must have a very long axial extension, i.e. a big overall size, which leads to bulky and large structures. The magnet in the outer ring being relatively big, it emits magnetic stray fields to the outside which may interfere with systems that work with electron beams, such as monitors or endoscopic cameras, or the like. In addition, the inner circular magnet is mechanically connected with two different components, namely the outer stationary sleeve with the helically shaped slot, and the blind bore in the inner mount of the optical system. In order to ensure jam-free operation, it is necessary to use precisely manufactured parts and also to provide a certain play with the result that especially reversing movements will lead to jerky movements with changes in adjustment of the optical system.

U.S. Pat. No. 5,359,992 describes a device for positioning components within endoscopic systems, where two diametrically opposite helically shaped slots are provided in the outer ring element in which diametrically opposite circular magnets are inserted. The circular magnets engage an axial directed recess in the outer side of a sleeve arranged in the ring. Rotation of the outer ring thus causes the outer magnet to move in axial direction. Inside the closed section, there are provided corresponding diametrically opposite magnets which follow the movements of the outer magnet, thereby effecting the coupling action. The inner set element, with the inner magnets, is not guided mechanically so that in the event the inner element should get out of the magnetic field of the outer magnet, due to a shock or some other impact, it can be moved toward and backward, and can be rotated inside the housing. In order to reestablish the proper function, the endoscope then has to be pivoted until the interaction between the outer and inner magnets has been reestablished.

A similar structure has been known from DE 88 10 044 U1, where a magnet arranged on the inner side of the outer ring interacts with an inner magnet of very long extension.

The outer magnet is moved in axial direction thereby entraining the inner magnet and effecting the coupling effect.

A telescope functioning according to that basic lens-adjusting principle has been known from German Patent Specification No. 970 298. Here again, there is a risk that mechanical shocks may bring the inner magnet out of magnetic interaction with the outer magnet.

SUMMARY OF THE INVENTION

It is therefore an object of the present invention to improve a device of the afore-mentioned kind in such a way that effective positioning of components and safe functioning can be permanently ensured with a structure of small overall size.

This object is achieved according to the invention, with regard to the device for positioning components within endoscopic systems of the type cited initially, by the fact that both, said outer and said inner ring element, are configured as rotatable, but axially nondisplaceable rings carrying oppositely arranged said magnets, and that said inner ring is mechanically connected with said components to be positioned.

The invention now deviates from the principle that at least one magnet, or even both, are movable in axial direction.

The system now only comprises rotatable rings that carry the magnets so that the axial extension of the magnetic coupling is relatively short. This on the one hand results in a relatively short overall length of the magnetic coupling, and avoids in addition large axial areas through which interfering magnetic fields might be emitted, so that any interfering radiation can be screened effectively, i.e. without extensive structures.

The relative position between the inner and the outer magnets does not change during rotation. When the outer ring is rotated together with the outer magnet, the inner ring with the inner magnet rotates correspondingly. Accordingly, the system does absolutely without any helically shaped guides for moving the magnets. Translation of the rotary movement of the inner ring is effected by the mechanical connection between the components to be positioned and the ring.

All in all, the mechanical coupling has a very short overall axial extension, and does with only two fundamental components, namely an outer ring with the at least one outer magnet and an inner ring with the at least one inner magnet, so that the constituent parts are little susceptible to faults and provide permanent functional safety. Due to the fact that the rings are axially fixed against displacement, mechanical shocks or impact cannot interrupt the magnetic coupling in the axial direction. The narrow overall size in axial direction permits magnetic screening to be realized by simple structural measures. And in the radial direction, the magnetic coupling also exhibits a moderate overall size, since the two rings, being arranged substantially in one plane, constitute components of relatively small size.

According to a further embodiment of the invention, the outer ring is provided on its outer side with a ferromagnetic screening in order to screen any interfering, outwardly directed magnetic stray fields.

This feature provides the advantage that the outer screening ensures that no interfering, outwardly directed stray fields will emanate from the magnetic coupling.

According to another embodiment of the invention, the outer ring is made from a ferromagnetic material with the at least one magnet mounted on its inner side.

This feature provides the advantage that the screening constitutes at the same time the carrier element and/or the ring on whose inner side the at least one magnet is mounted.

This also leads to structurally simple parts of small overall size.

According to a further embodiment of the invention, a plurality of radially polarized magnets are mounted on the inner side of the outer ring, in circumferentially distributed arrangement.

By arranging a plurality of radially polarized magnets it is possible to give the ring an extremely narrow design in axial direction as the plurality of the magnets permit the necessary coupling with the inner magnet to be achieved in any rotary position.

According to a further embodiment of the invention, the outer ring is configured as a set collar.

This feature provides the advantage that the outer ring acts simultaneously as set collar, i.e. that the latter can be gripped from the outer side, which means that an especially small number of components is required, which in turn leads to a narrow structure also in radial direction.

According to a further embodiment of the invention, the outer ring is connected on its outer side with a set collar.

This feature provides the advantage that the materials of the outer ring and of the set collar surrounding the latter can be freely selected so that special demands placed on the design can be met in case, for example, it should be desired to adapt the outer design of the set collar to the outer design of the remaining endoscopic system. There is further the possibility to have the set collar simultaneously perform the function of the screening, and to make the inner ring for example from a plastic material with the magnets embedded therein. The outer ring can be rotated manually, or can be driven via a motor, especially an electric motor.

According to a further embodiment of the invention, a plurality of radially polarized magnets are provided on the outer side of the inner ring in circumferentially distributed arrangement.

This feature provides the considerable advantage, especially in combination with the previously mentioned feature relating to the plurality of magnets provided on the inner side of the outer ring, that a coupling effect sufficient to move even relatively heavy or heavy-moving components can be ensured with rings of extremely narrow axial overall size. This further contributes to a relatively small structure, i.e. a narrow structure in both the axial and the radial direction.

According to a further embodiment of the invention, the number, circumferential distribution and axial extension of the magnets are equal for the inner and the outer ring.

This feature provides the considerable advantage that an intense magnetic flux occurs between the individual identical oppositely arranged magnets so that no relative displacements between the outer and the inner ring will occur even if the outer ring should be moved abruptly or insensitively. This contributes significantly toward increasing the operating safety.

According to another embodiment of the invention, the inner ring is connected, via a thread, with a component arranged for axial displacement in the housing so that any rotary movement of the inner ring will be translated into an axial movement of the component.

This feature provides the advantage that the rotary movement of the inner ring can be translated by simple mechanical means to an axial movement of the component.

According to a further embodiment of the invention, the axially movable component is protected against rotary movement.

This feature provides the advantage, especially in the case of optical systems, that the latter will be moved only in axial direction, without being rotated, which in the case of complex optical systems, especially in the case of non-spherical lenses, could result in optical displacements.

According to a further embodiment of the invention, the axially displaceable component is subjected to the force of a spring in the axial direction.

This feature provides the advantage that the play of the mechanical translation of the rotary movement to an axial movement, necessarily existing, is permitted to occur, by the force of the spring, only in a very defined end position of the play, and that the reversal of the axial displacement is likewise effected in a jerk-free and smooth elastic fashion.

According to a further embodiment of the invention, the inner ring carries components that can be swung into and out of an optical system by rotation of the inner ring.

This feature provides the considerable advantage that components such as filters, screens, diaphragms, or the like, can be laterally swung into and out of an optical system by means of the magnetic coupling. The rotary axis of the rings does not coincide with the optical axis in this case. The components are swung into and out of the optical system in the way of a revolver magazine.

According to a further embodiment of the invention, the range of rotation of the outer ring is limited.

This feature, which is known as such, provides the advantage that any excessive rotation is rendered impossible.

According to a further embodiment of the invention, the magnets are designed as Sm—Co magnets, comprising preferably an alloy of $SmCo_5$ and/or $Sm_2Co_{17}$ based on ferrous metal.

This feature provides the advantage that such Samarium-Cobalt magnets are highly temperature-resistant up to 200° Celsius. The extreme temperature variations to which endoscopic systems are exposed during autoclaving do not impair the magnetization.

It is understood that the features mentioned above and those yet to be explained below can be used not only in the respective combinations indicated, but also in other combinations or in isolation, without leaving the context of the present invention.

The invention will be described in more detail and explained below with reference to certain selected exemplifying embodiments. In the drawings:

DETAILED DESCRIPTION OF PREFERRED EMBODIMENTS

Figure 1:
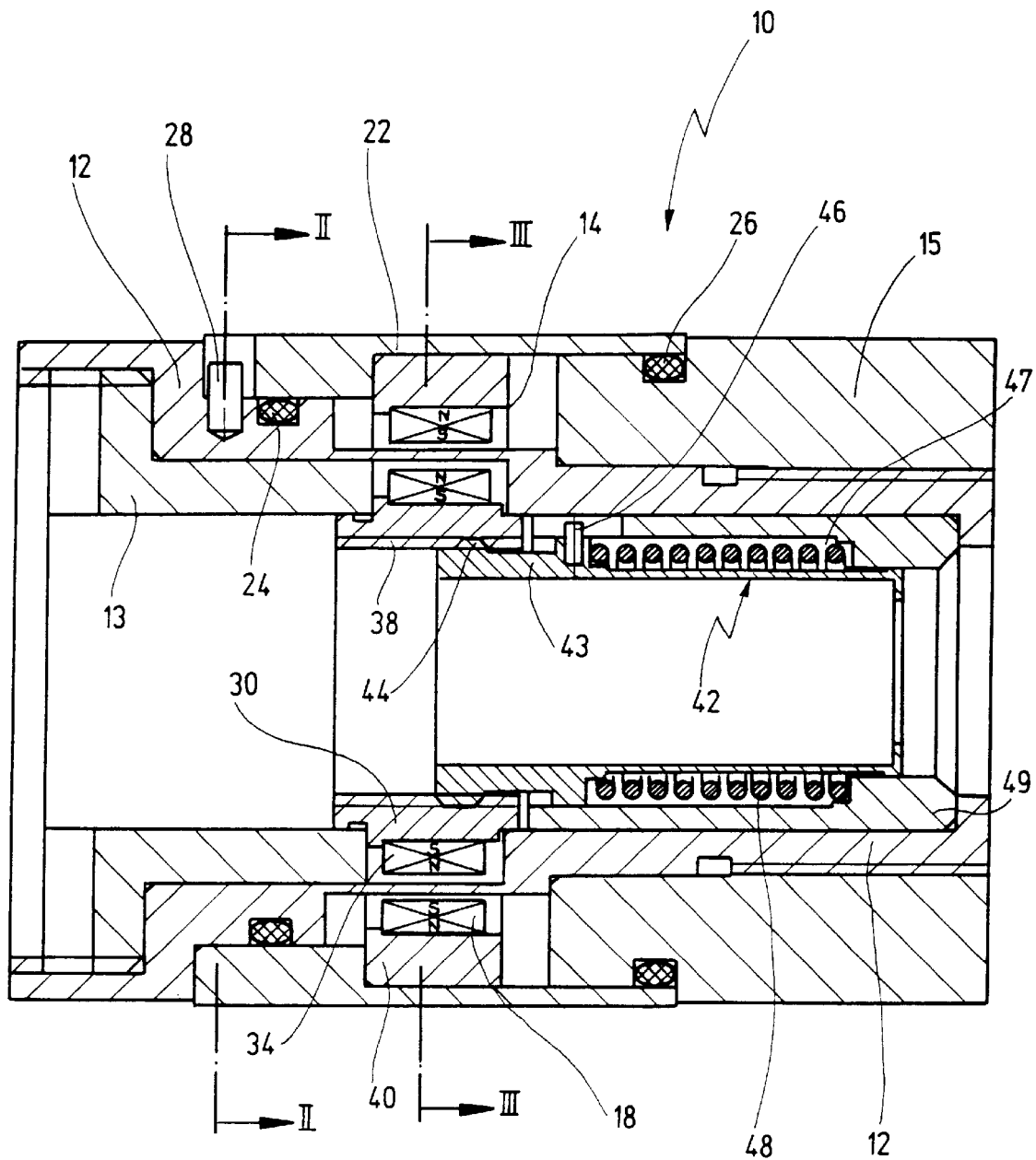
FIG. 1 shows a longitudinal section through a device according to the invention for axially positioning optical components.
Figure 2:
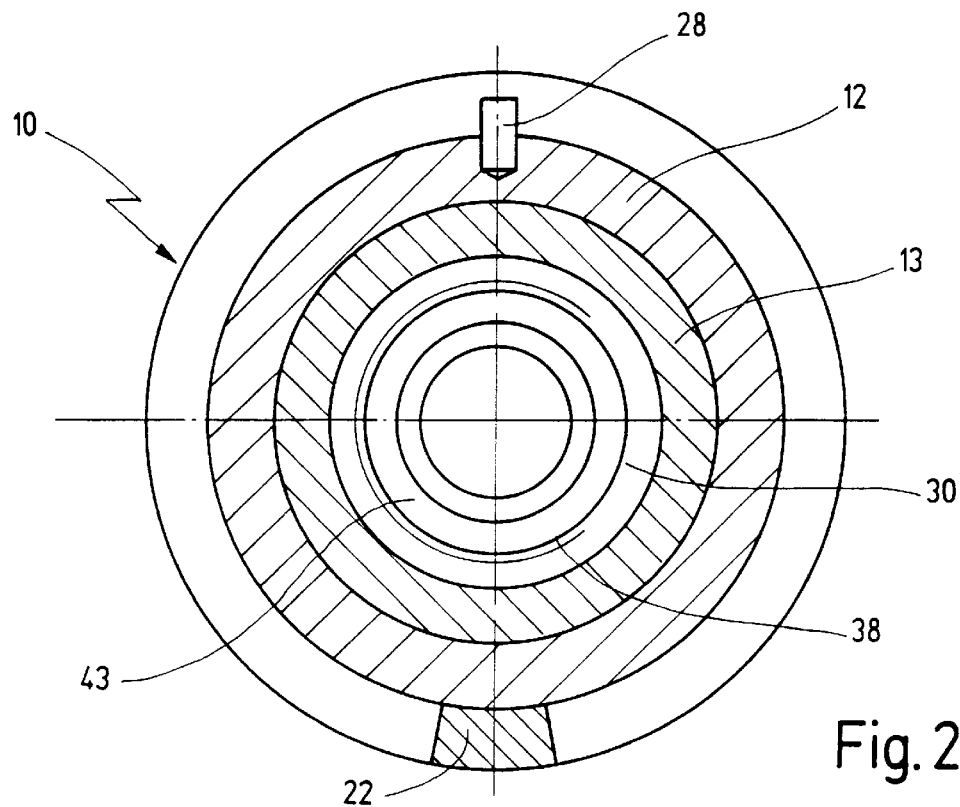
FIG. 2 shows a sectional view, taken along line II—II in FIG. 1.
Figure 3:
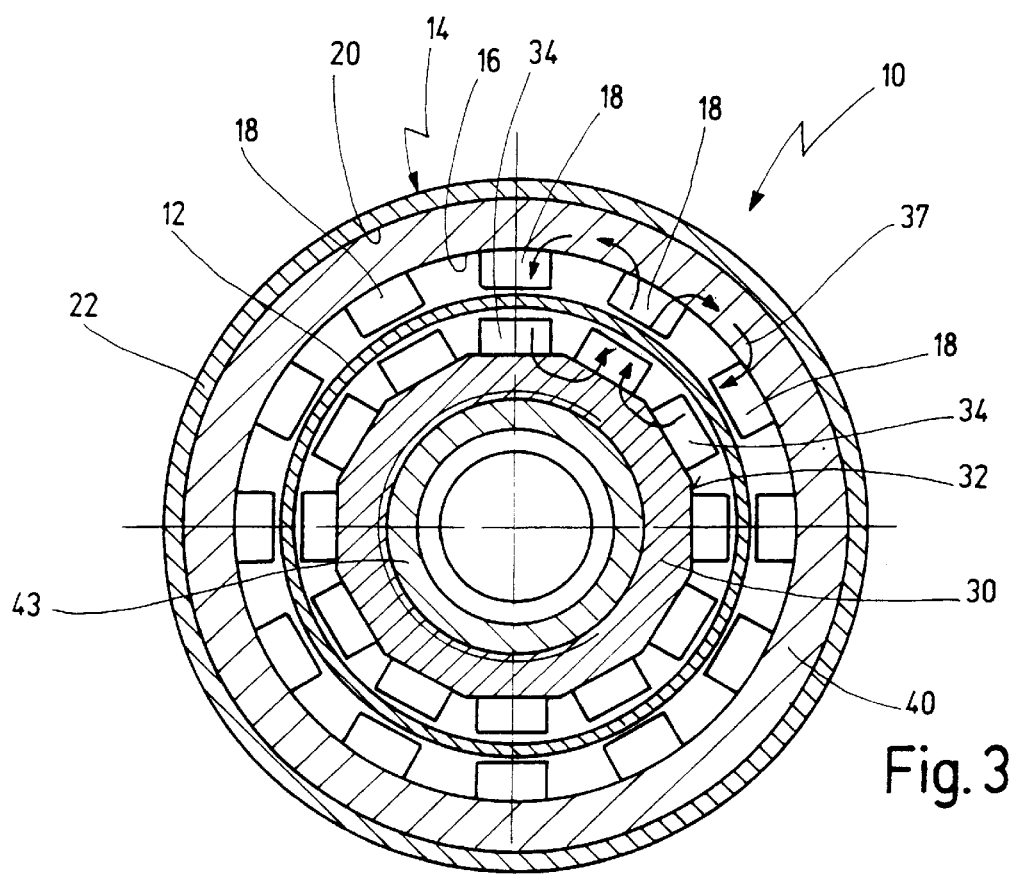
FIG. 3 shows a sectional view, taken along line III—III in FIG. 1.

A device illustrated in FIGS. 1 to 3 is indicated generally by reference numeral 10.

Device 10 is part of an optical head of an endoscope, which is followed at the right—as viewed in FIG. 1—by an eyepiece cup, not shown in the drawing for the sake of clarity, and at the left—as viewed in FIG. 1—by the shaft of an endoscope.

Device 10 comprises a roughly hollow-cylindrical housing 12, consisting peripherally of a single piece and being, thus, hermetically sealed.

End faces of housing 12 are correspondingly sealed by the before-mentioned components, i.e. the eyepiece cup on the one hand and the endoscope shaft on the other hand.

An inner mounting sleeve 13 and an outer mounting sleeve 15 serve as mounting elements for the elements that are received in housing 12 and that will be described in more detail hereafter.

An outer ring 14, slid over the outer side of housing 12, is provided on its inner side 16 with twelve outer radially polarized circular magnets 18 evenly distributed over its circumference. As can be seen best in the sectional view of FIG. 3, the inner face of magnets 18 comes to lie a very small distance away from the outer side of housing 12.

Mounted on an outer side 20 of outer ring 14 is a set collar 22, which has an axial length considerably greater than outer ring 14 and which is mounted, via O-ring seals 24 and 26, in sealing but rotatable relationship on the outer side of housing 12. A radially projecting stop 28 provided in housing 12 limits the circumferential rotary movement of outer ring 14, as can be seen best in FIG. 2.

Inside housing 12, there is provided an inner ring 30 whose outer side 32 is likewise provided with twelve inner circular magnets 34.

As can be seen best in the sectional view of FIG. 3, the circumferential distribution and arrangement of magnets 34 is selected in such a way that each inner magnet 34 is arranged directly opposite a corresponding outer magnet 18. The outer side of magnets 34 extends almost to the inner side of housing 12.

Thus, the magnets are arranged at extremely small radial distances one from the other, being however separated one from the other by hermetically sealed housing 12. Magnets 34 are likewise radially polarized, their polarity being directed in such a way (see FIGS. 1 and 3) that a magnetic flux occurs, as indicated by lines 37 in FIG. 3. Magnets 18 and 34 are realized as SmCo magnets.

In the illustrated embodiment, outer ring 14 consists of a ferromagnetic material, thus forming a screen 40 relative to the outside. This means that no magnetic fields leak to the outside. The ferromagnetic material thus presents a considerably smaller magnetic resistance relative to the outside, i.e. to the air, so that almost the entirety of the outer magnetic flux flows through screen 40.

Inside housing 12, there is arranged a component 42 comprising a sleeve 43. Inside sleeve 43, there are arranged optical components, such as lenses, which are not shown in the drawing for the sake of clarity.

The outer side of sleeve 43 is provided with a radially projecting lug 44 that engages a thread 38 on inner side 36 of inner ring 30.

A pin 46, projecting radially from outer side 47 of sleeve 43, serves as protection against rotation and engages a corresponding axial groove—not indicated in detail—in an outer sleeve 49 surrounding sleeve 43.

Accommodated in the space between outer sleeve 49 and sleeve 43 is a biased helically shaped spring 48 that acts in axial direction upon axially displaceable sleeve 43 relative to stationary outer sleeve 49.

Now, when outer ring 14 is rotated via set collar 22, the coupling effect between magnets 18 and 30 causes inner ring 30 to be rotated as well. This rotary motion is translated to an axial displacement of sleeve 43 via thread 38 and lug 44.

It is possible in this way to displace, for example adjust or focus, the optical components received in sleeve 43 relative to other components received in the optical head.

Figure 4:
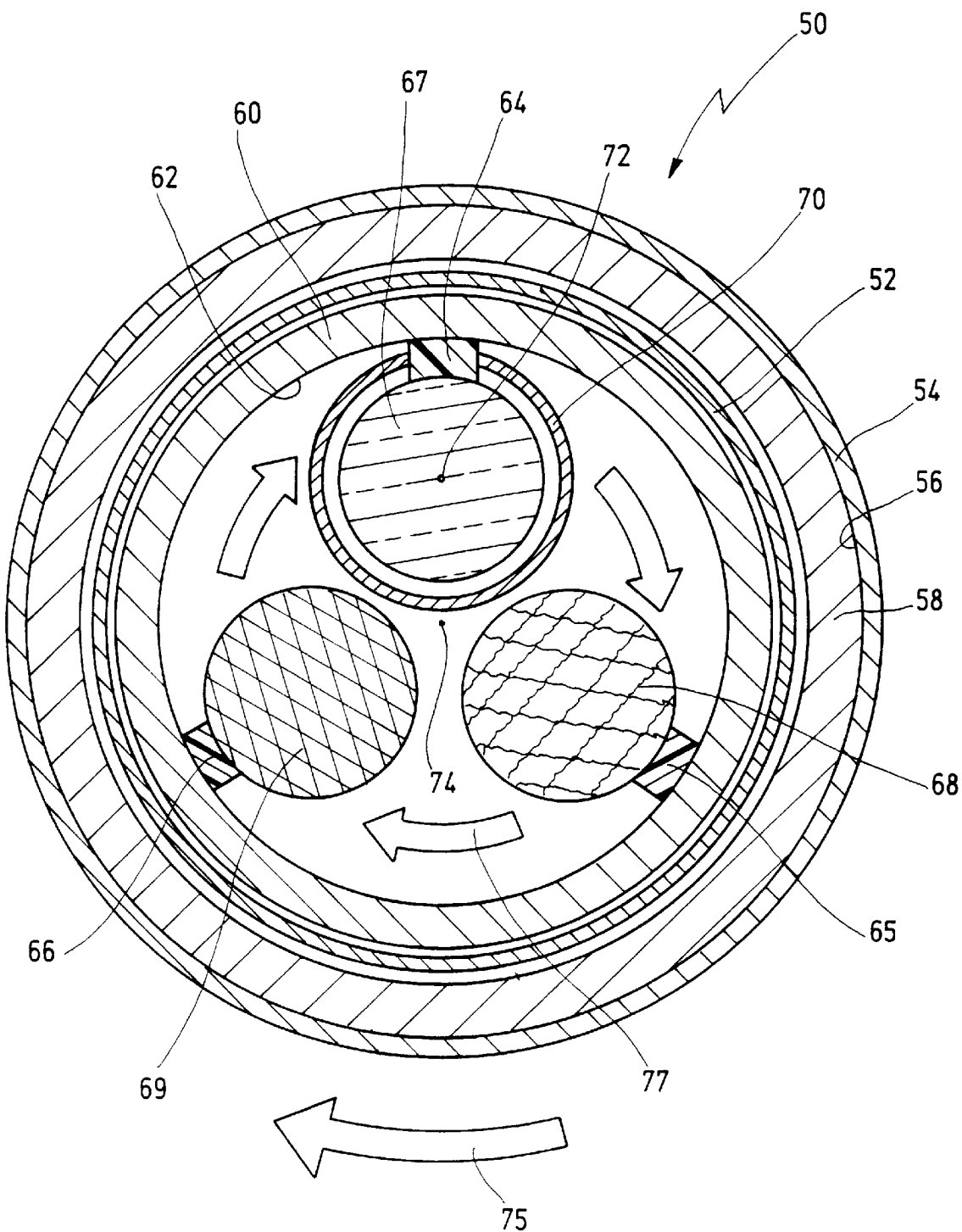
FIG. 4 shows a cross-section through another embodiment of a device according to the invention for circumferentially positioning components in an optical system and for swinging them into and out of the latter.

FIG. 4 illustrates a further embodiment of a device 50 according to the invention, which likewise comprises a cylindrical, hermetically sealed housing 52 closed on its end by further components. Housing 52 is surrounded by an outer ring 54 that carries a ring magnet 58 on its inner side 56.

Correspondingly, an inner ring 60, designed itself as ring magnet, is arranged inside housing 52.

Three radially projecting carriers 64, 65, 66, each carrying components 67, 68, 69, project from the inner side of inner ring 60 at positions spaced about its circumference by 120° each.

Component 67 may for example be a lens, component 68 a filter, component 69 a polarizer.

Housing 52 accommodates in its inner space an optical system whose optical axis 72 is offset from longitudinal center axis 74 of cylindrical housing 52.

The centers, not specifically indicated in the drawing, of substantially circular components 67, 68, 69 are arranged in such a way that they coincide with a peripheral circle whose radius corresponds to the spacing between longitudinal center axis 74 and optical axis 72.

Now, when outer ring 54, which may be configured as a set collar, or which may also comprise the screening described above, is rotated as indicated by arrow 75, inner ring 60 will be rotated correspondingly, as indicated by arrows 77.

In the rotary position illustrated in FIG. 4, optical component 70 has just been pivoted exactly into the optical path of optical system 70.

By rotating outer ring 54 by further 120° in clockwise direction, component 67 is then swung out from optical system 70, whereas component 69 is swung in. Rotation in the opposite direction, or further rotation by 120° then causes component 68 to be swung in correspondingly.

Of course, optical system 70 may be equipped with the device described above with reference to FIGS. 1 and 3 at a different axial position, for carrying out for example focusing or adjusting operations, and may of course in addition comprise device 50 for swinging other systems in and out. Due to the very short structure, in the axial direction, it is thus possible to provide both a device 10 and a device 50 on one and the same optical instrument.

In the embodiment described with reference to FIG. 4, components 67, 68, 69 lie substantially in one plane.

However, it is of course also possible to provide them in axially offset arrangement, in which case they will be arranged on the inner side of a component, as is for example sleeve 43 illustrated in FIG. 1. Rotary movement of outer ring 54 then effects a circumferential rotation and, simultaneously, an axial movement of the elements to be swung out from or into optical system 70. This will be the case when the components to be swung in have a greater radial extension, i.e. when there is not sufficient room in one plane to accommodate them, as indicated in FIG. 4.

What is claimed, is:

1. A device for positioning components within endoscopic systems, comprising:

a housing hermetically sealed and having an outer side;

an outer ring element mounted to rotate about said outer side of said housing and carrying on its circumference at least one outer magnet;

an inner ring element mounted inside said housing and carrying at least one inner magnet;

a component positioned inside said housing;

said at least one inner magnet and said at least one outer magnet being arranged such that any rotation of said outer ring element effects movement of said at least one inner magnet by magnetic coupling, such movement serving the purpose to axially position said component;

wherein said outer and said inner ring elements, are configured as rotatable, but axially nondisplaceable rings carrying oppositely arranged said at least one inner magnet and said at least one outer magnet;

wherein said inner ring is mechanically connectable with said component to be positioned; and wherein said inner ring is connectable, via a thread, with said component arranged for axial displacement in said housing so that any rotary movement of said inner ring will be translated into an axial movement of said component.

2. The device of claim 1, wherein said axially movable component is protected against rotary movement.

3. The device of claim 2, wherein said axially displaceable component is subjected to the force of a spring in the axial direction.

4. The device of claim 2, wherein said at least one inner magnet and said at least one outer magnet are Sm—Co magnets.

5. The device of claim 1, wherein said at least one inner magnet and said at least one outer magnet are Sm—Co magnets.

6. A device for positioning components within endoscopic systems, comprising:

a housing hermetically sealed and having an outer side;

an outer ring element mounted to rotate about said outer side of said housing and carrying on its circumference at least one outer magnet;

an inner ring element mounted inside said housing and carrying at least one inner magnet;

a component positioned inside said housing;

said at least one inner magnet and said at least one outer magnet being arranged such that any rotation of said outer ring element effects movement of said at least one inner magnet by magnetic coupling, such movement serving the purpose to axially position said respective components;

wherein said outer and said inner ring elements, are configured as rotatable, but axially nondisplaceable rings carrying oppositely arranged said at least one inner magnet and said at least one outer magnet;

and wherein said inner ring is mechanically connectable with said components to be positioned; and wherein said inner ring is connectable, via a thread, with said component arranged for axial displacement in said housing so that any rotary movement of said inner ring will be translated into an axial movement of said component, and wherein said axially displaceable component is subjected to the force of a spring in the axial direction.

7. The device of claim 6, wherein said inner ring carries said component that can be swung into and out of an optical system by rotation of said inner ring.

8. The device of claim 7, wherein the range of rotation of said outer ring is limited.

9. The device of claim 6, wherein said at least one inner magnet and said at least one outer magnet are Sm—Co magnets.

10. The device of claim 6, wherein said at least one inner magnet and said at least one outer magnet comprise an alloy of $Sm_2Co_{17}$.

11. The device of claim 6, wherein said at least one inner magnet and said at least one outer magnet comprise an alloy of $SmCo_5$ and $Sm_2Co_{17}$.

12. The device of claim 6, wherein said at least one inner magnet and said at least one outer magnet comprise an alloy of $SmCo_5$.

* * * * *